United States Patent [19]

Frieze et al.

[11] Patent Number: 5,755,719
[45] Date of Patent: May 26, 1998

[54] ACETABULAR REAMER

[75] Inventors: Allan S. Frieze, Alpine; David Nalepa, Jersey City; Thomas Abraham, Rutherford, all of N.J.

[73] Assignee: Case Medical, Inc., Ridgefield, N.J.

[21] Appl. No.: 784,005

[22] Filed: Jan. 15, 1997

[51] Int. Cl.[6] ............................................. A61B 17/56
[52] U.S. Cl. ............................................................ 606/81
[58] Field of Search ................................. 606/79, 80, 81, 606/82, 83, 84, 85, 86, 87, 88, 89

[56] References Cited

U.S. PATENT DOCUMENTS

| | | |
|---|---|---|
| 3,554,192 | 1/1971 | Isberner . |
| 3,633,583 | 1/1972 | Fishbein . |
| 4,621,637 | 11/1986 | Fishbein . |
| 5,100,267 | 3/1992 | Salyer . |
| 5,116,165 | 5/1992 | Salyer . |
| 5,122,134 | 6/1992 | Borzone et al. . |
| 5,180,384 | 1/1993 | Mikhail . |
| 5,192,291 | 3/1993 | Pannek, Jr. . |
| 5,203,653 | 4/1993 | Kudla ........................... 606/81 |
| 5,222,959 | 6/1993 | Anis . |
| 5,318,576 | 6/1994 | Plassche et al. . |
| 5,376,092 | 12/1994 | Hein et al. . |

FOREIGN PATENT DOCUMENTS

| | | |
|---|---|---|
| 1031888 | 6/1953 | France . |
| 1041311 | 10/1953 | France . |
| 2233972 | 1/1975 | France . |
| 1225-543-A | 4/1986 | U.S.S.R. . |

*Primary Examiner*—Guy V. Tucker
*Attorney, Agent, or Firm*—Woodbridge & Associates

[57] ABSTRACT

An acetabular reamer includes a base, a first set of semi-circular blades attached to the base, and a second set of semi-circular blades also contacting said base, and crossing and intersecting with said first set of blades at right angles thereto. The base preferably comprises a circular plate having a hexagonal drive hole in the center thereof and a plurality of slots in the periphery thereof for anchoring the blades. Each semi-circular blade includes a first end having a projection thereon, a second end opposite from said first end and also having a projection thereon, a first edge having serrated cutting teeth thereon, a second edge opposite from said first edge, and a first and second side surface. The cutting edge of the first set of blades includes a plurality of outwardly facing slots which mate with and engage a second set of inwardly facing slots in the second edge of said second blades. When the first and second set of blades are assembled in this fashion the cutting edges of both sets of blades lie in the same spherical plane. The projections can comprise snap-in projections that automatically lock in position or projections that can be twisted and locked into position. Alternatively, the base can comprise a pair of upper and lower plates with apertures in the upper plate such that when the blade projections mate with the apertures, riveting of the lower plate with respect to the upper plate locks the projections and their related blades into position on the base. When the reamer is assembled it has a hemispherical shape suitable for reaming the acetabulum of the hip so that the acetabular portion of a hip implant properly fits into the acetabulum.

15 Claims, 8 Drawing Sheets

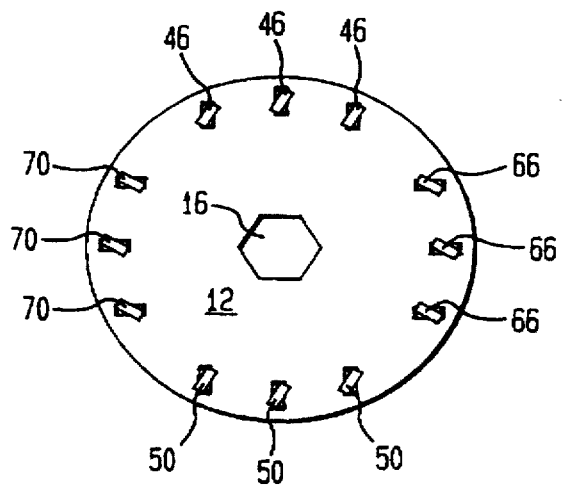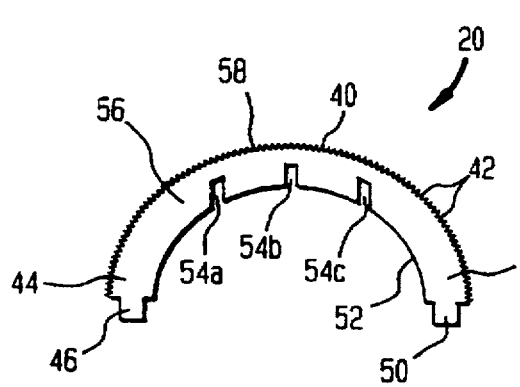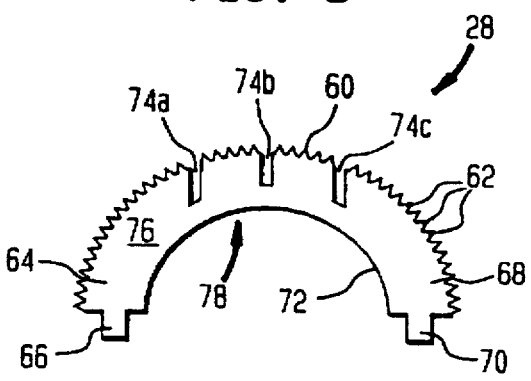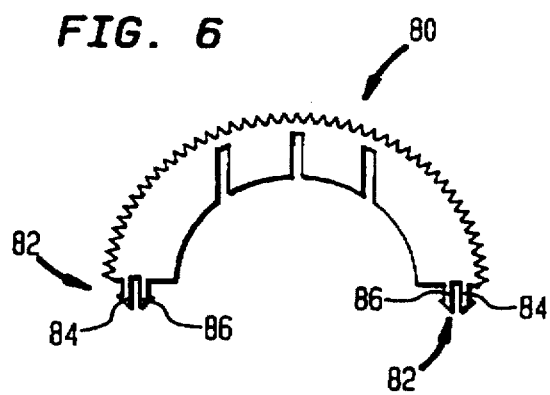

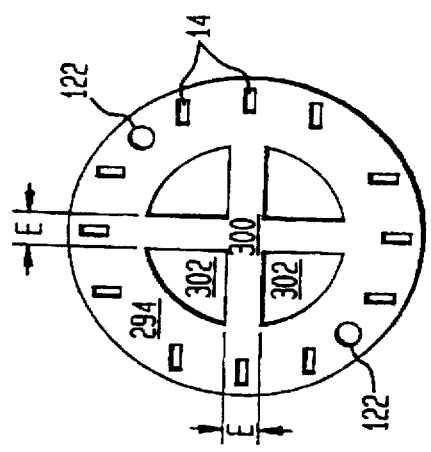
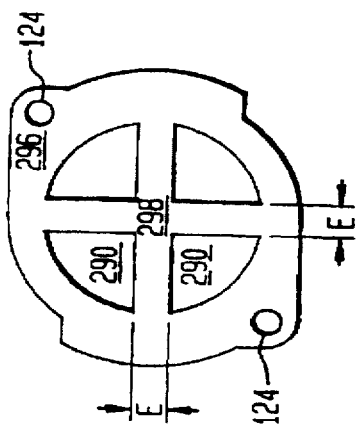
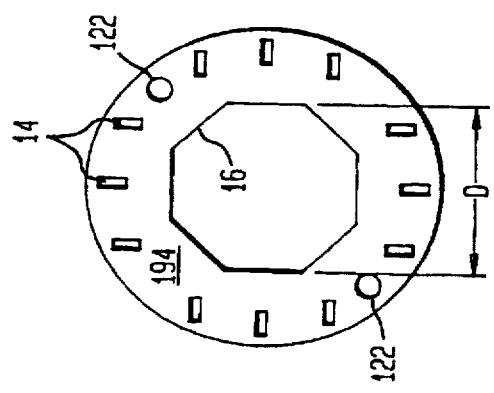
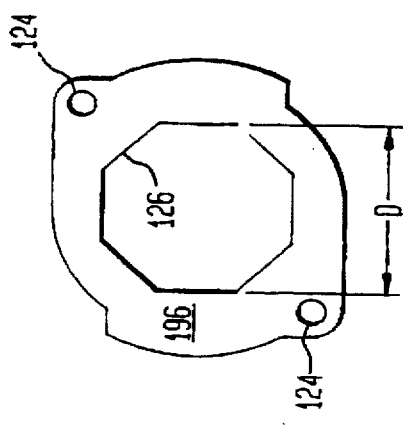
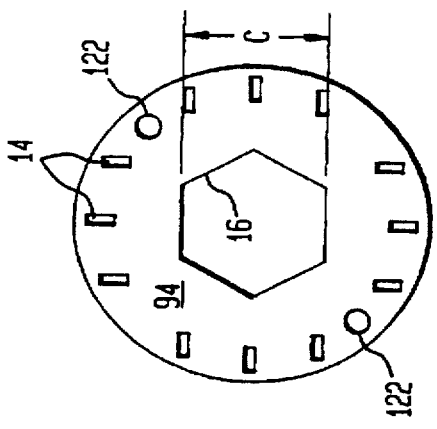
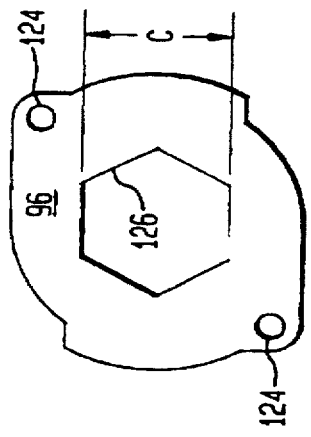

ACETABULAR REAMER

BACKGROUND OF THE INVENTION

1. Field of the Invention

The invention relates to a multi-blade acetabular reamer and a method for constructing the same.

2. Description of Related Art

The prior art patent literature describes a few reamers and cutters for removing bone and tissue from joints that may be relevant to the state of the art. For example, U.S. Pat. No. 4,621,637 entitled "SURGICAL DEVICE FOR REMOVING BONE AND TISSUE FROM JOINT MEMBERS" teaches a slotted, surgical device including a hemispheric housing that supports one or more cutting blades for bone and/or tissue cutting. Two and three blade embodiments are described. In both cases, the blades abut centrally of the device and interlock with the base at discrete points.

French Patent 1,031,888 describes a plurality of cutting blades which are radially disposed, equiangularly spaced atop a supporting plate and locked to the plate by fasteners. The resulting tool is used for cutting the acetabular portion of a hip prior to joint replacement.

Similarly, French Patent 1,041,311 describes a bone cavity forming tool which employs multiple blades in a hemispheric array.

Soviet Union Patent 1225-543-A entitled "BONE CUTTING TOOL FOR SURGERY" describes a cutter comprising multiple arcuate cutting elements extending from a central rod outwardly in an umbrella fashion.

French Patent 2,233,972 entitled "ARTIFICIAL HIP JOINT FITTING EQUIPMENT" describes another multi-blade, round headed milling cutter for acetabular application.

U.S. Pat. No. 5,222,959 entitled "REMOVAL OF TISSUE" describes a soft tissue cutter having an oval, rather than hemispheric, shape.

U.S. Pat. No. 5,192,291 entitled "ROTATIONALLY EXPANDABLE ATHERECTOMY CUTTER ASSEMBLY" describes another soft tissue cutter in which the blades define a cylindrical, not hemispheric, structure.

U.S. Pat. No. 5,100,267 entitled "DISPOSABLE ACETABULAR REAMER CUP" describes a hemispheric, cup-shaped hip reamer. With regard to this structure, note also U.S. Pat. Nos. 5,116,165 and 5,376,092.

The following U.S. Patents describe prior art bone reamers of possible interest, using multi-blade configurations, but for non-hip applications: 3,554,192; 5,122,134, 5,180,384 and 5,318,576.

Lastly, U.S. Pat. No. 3,633,583 entitled "ORTHOPEDIC SINGLE-BLADE BONE CUTTER" is of general relevance only.

While a few joint reamers are known in the prior art, they tend to be expensive, or hard to construct, or both. There clearly appears to be a need for a safe, easy to assemble, inexpensive and effective reamer especially for the acetabulum of the hip. Insofar as understood, none of the prior art known to the inventor, whether taken individually or in combination, hints, teaches or suggests the novel acetabular reamer disclosed herein.

SUMMARY OF THE INVENTION

Briefly described, the invention comprises an acetabular reamer including a base, a first set of three semi-circular blades attached to the base, and a second set of three semi-circular blades also attached to the base, but at right angles to said first set of blades. The first set of three blades includes a major blade that spans the entire diameter of the circular base, and a pair of smaller, minor blades, that span a shorter chord of the circular base. Likewise, the second set of blades includes a major blade that spans the greater diameter of the circular base and a pair of smaller, minor blades that span a lesser chord. Each of the semi-circular blades includes a first and a second end, an exterior cutting edge, an interior edge opposite from said cutting edge, and a pair of side faces. The first and second end of each of the blades includes a projection which is receivable in a slotted aperture on the periphery of the circular base. Each of the three blades of the first set of blades includes three slots on the outer cutting edge thereof which engage respectively with one of three slots located on the interior edge of each of the three blades of the second set. The apparatus is first assembled by engaging the slots of the first set of three blades with the slots of the second set of three blades so that the ultimate structure has a three dimensional shape and the cutting surfaces of said first and second set of blades are at the same level where said blades intersect.

According to the preferred embodiment of the invention, the projections on the blades include a pair of prongs that snap and lock into the peripheral apertures on the base. According to an alternative embodiment of the invention the projections, or tabs, extend through the apertures in the base and can be locked in place by twisting them with respect to their respective slots so they cannot back out. According to another embodiment of the invention, the base comprises a pair of upper and lower plates wherein the lower plate locks the projections into the peripheral slots of the upper plate.

These and other features of the invention will be more fully understood by reference to the following drawings.

BRIEF DESCRIPTION OF THE DRAWINGS

FIG. 3 is a bottom plan view of the base of the preferred embodiment illustrated in FIG. 1.

FIG. 4 illustrates the largest of the cutter blades having inwardly facing slots according to the preferred embodiment of the invention.

FIG. 5 illustrates the largest of the cutter blades having outwardly facing slots according to the preferred embodiment of the invention.

FIG. 6 illustrates a blade according to a first alternative embodiment of the invention in which the cutting blades are anchored and locked into position in the peripheral slots in the base by a pair of projections each including a pair of spring loaded elements.

FIG. 12A is a bottom plan view of the upper, or top base plate according to the embodiment illustrated in FIGS. 7–10B.

FIG. 12B is a bottom plan view of the bottom, or lower base plate of the embodiment illustrated in FIGS. 7–10B.

FIG. 12C illustrates another, upper base plate suitable for use with the embodiment of FIG. 7–10B but including a larger, central, hexagonal drive hole.

FIG. 12D illustrates another, lower, base plate suitable for use with the embodiment illustrated in FIG. 7–10B but including a larger, central, hexagonal drive hole that matches the drive hole of the upper plate illustrated in FIG. 12C.

FIG. 12E illustrates another, upper base plate suitable for use with the embodiment of FIG. 7–10B but including an X-shaped center.

FIG. 12F illustrates a bottom, or lower plate suitable for use with the embodiment of FIG. 7–12B, and including an X-shaped central drive section complimentary to the X-shaped drive section of the upper base illustrated in FIG. 12E.

DETAILED DESCRIPTION OF THE INVENTION

During the course of this description like numbers will be used to identify like elements according to the different figures that illustrate the invention.

Figure 1:
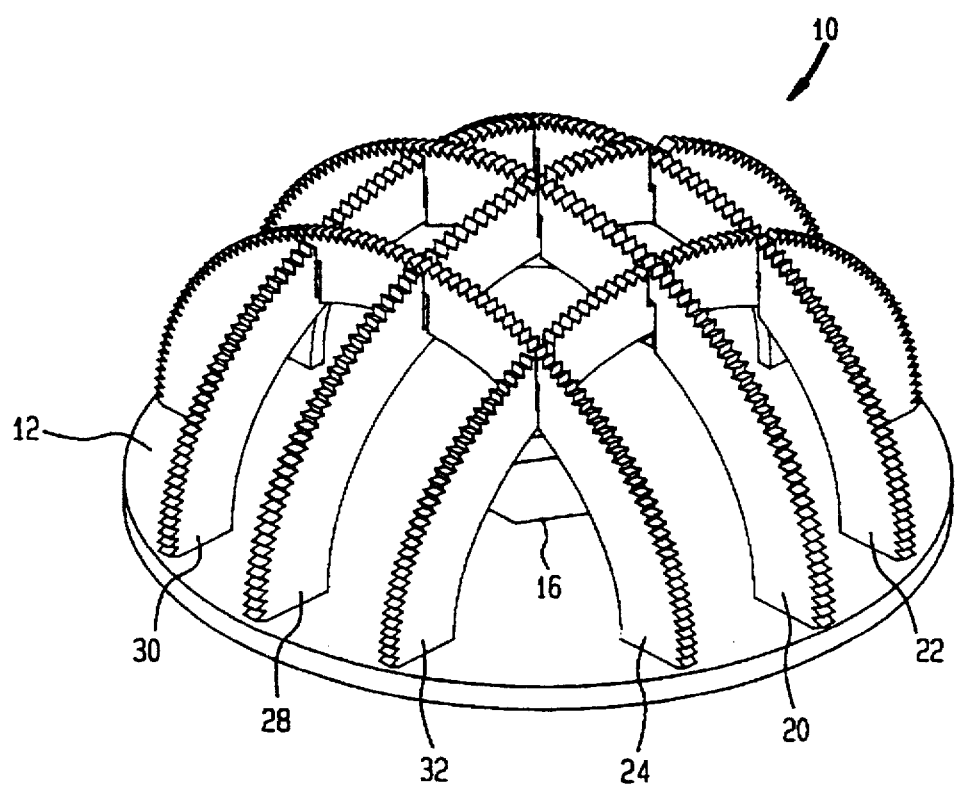
FIG. 1 is a perspective view of the preferred embodiment of the acetabular reamer invention.
Figure 2:
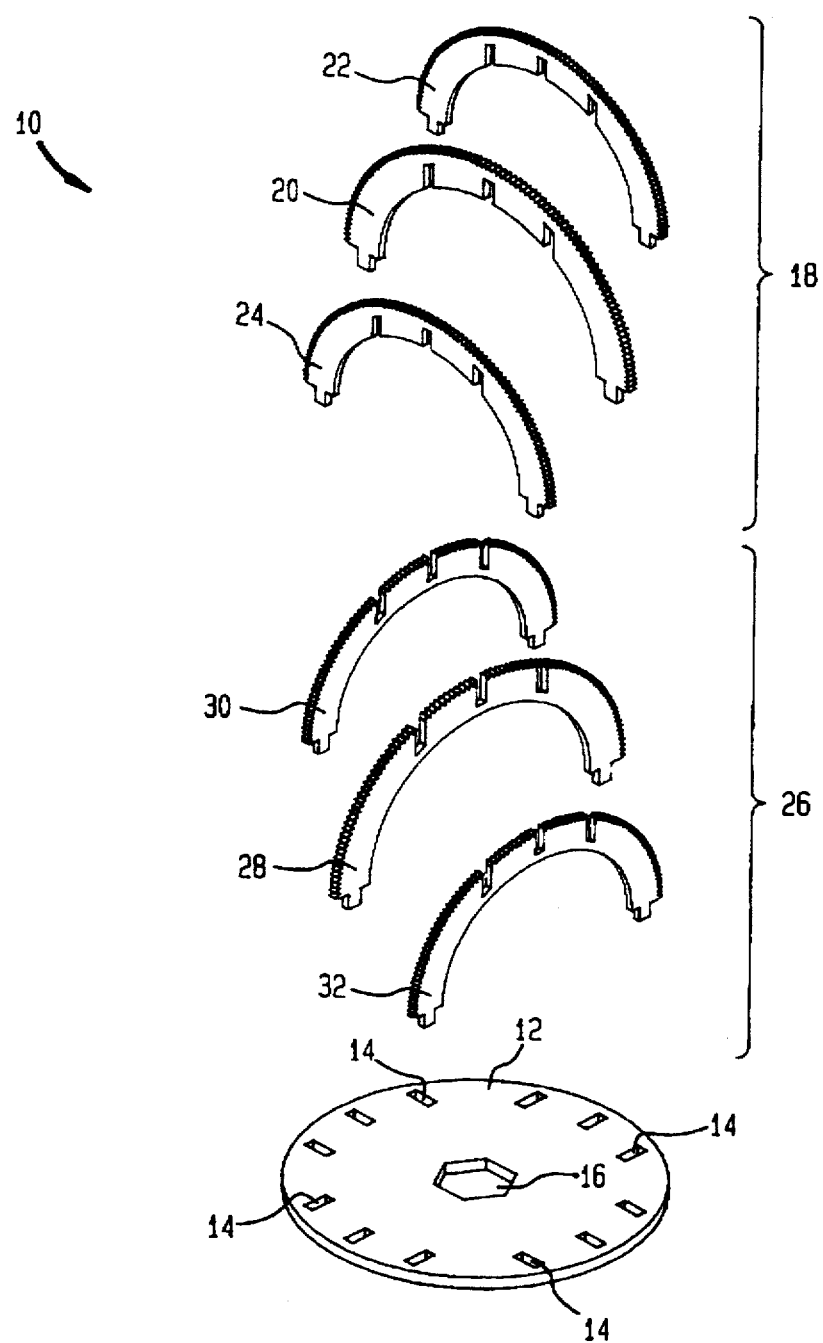
FIG. 2 is an exploded view of the preferred embodiment illustrated in FIG. 1.

The preferred embodiment 10 of the invention is illustrated in its assembled form in FIG. 1 and in an exploded form in FIG. 2. The basic elements of the preferred embodiment 10 are a base 12, a first set 18 of cutter blades (20, 22, 24) and a second set 26 of mating cutter blades (28, 30, 32). The base 12, as seen in FIGS. 2 and 3, includes twelve peripheral slots 14 and a hexagonal center hole 16 suitable for mounting the acetabular reamer 10 on a drill. Slots 14 are arranged in four groups of three set at 90° with respect to each other.

The first group 18 of blades includes a larger cutter blade 20 that substantially spans the longest dimension, i.e., the diameter, of base 12. A pair of smaller, minor cutter blades 22 and 24 are located on opposite sides of the larger blade 20, and dissect a smaller chord of the circular base 12.

FIG. 4 illustrates the larger cutter blade 20 in greater detail. Smaller blades 22 and 24 are not illustrated because they both have a substantially identical shape. Larger cutter blade 20 includes a first, outwardly facing edge 40 including a plurality of serrated teeth 42. The size and dimension of teeth 42 may vary depending upon the nature of the hip socket that needs to be reamed. Large blade 20 also includes a first end 44 having a projection, or tab, 46 thereon and a second end 48 opposite, or distal from the first end 44 also including a tab or projection 50 thereon. Tabs 46 and 50 engage with, and pass through, a pair of slots 14 on opposite sides of base 12. Blade 20 also has a second edge 52, opposite the first edge 40, that includes three inwardly facing slots 54a, 54b and 54c. The remaining two blades 22 and 24 of the first group 18 also include three inwardly facing slots similar to slots 54a, 54b and 54c of blade 20. Lastly, blade 20 includes a first broad side face 56 and a second broad side face 58 on the opposite surface from face 56. Similarly, smaller blades 22 and 24 also include opposing broad side faces.

The largest cutter blade 28, from the second group of blades 26 is illustrated in FIG. 5. Like blade 20, blade 28 includes a first edge 60 including a plurality of sharp cutter teeth 62 opposite from an inwardly facing edge 72. Blade 28 further includes a first end 64 having a locking tab 66 and a second end 68, opposite, or distal from, the first end 64 also including a locking tab 70. A first broad, side face 76 is located opposite from a second broad side face 78. Large blade 28 further includes three outwardly facing slots 74a, 74b and 74c. Blades 30 and 32, of second group 26, also include three slots, respectively, similar in shape and location to slots 74a, 74b and 74c of blade 28.

When the acetabular reamer 10 is assembled the three blades 20, 22 and 24 from the first group 18 are placed over the blades 28, 30 and 32 of the second group 26 so that one slot 54a, 54b or 54c from a blade in the first group 18 matches and mates with a second slot 74a, 74b or 74c from a blade in the second group 26. For example, inwardly facing slot 54b of blade 26 mates with and engages with outwardly facing slot 74b of blade 28. Once the blades 20, 22, 24, 28, 30 and 32 have been mated and matched, they form an egg crate-like cross section in which the teeth 42 and 62 on the exterior edges 40 and 60 all lie in the same spherical plane. When assembled in this fashion, the locking tabs 46, 50, 66 and 70 line up with, and pass through, the peripheral slots 14 in the base 12. Once the tabs 46, 50, 66 and 70 pass through their respective slots 14 they can be twisted, and locked, in position as illustrate in FIG. 3. The reamer 10 can then be placed on an appropriate drill bit and rotated at the desired speed to ream a socket in the hip bone of a patient.

The method of assembly just described is relatively fast and economical. The reamer blades 20, 22, 24, 28, 30 and 32 can be cut with conventional laser equipment from medical grade steel. Fabrication and assembly can be performed in a matter of a few minutes.

FIG. 6 illustrates a first alternative embodiment 80 of a snap-in cutter blade. Snap-in cutter blade 80 includes a pair of resilient projections, or tabs, 82, located on the first and second end thereof. Each tab 82 includes a pair of opposite facing, L shaped elements 84 and 86. The remaining five blades of the group have tabs similar to 82. Once the six cutter blades have been assembled in the manner previously described with reference to the preferred embodiment 10, the tabs 82 are placed into peripheral slots 14. When the tabs 82 are forced into slots 14 they eventually snap into place thereby locking the six blades securely in position on the base 12.

Figure 7:
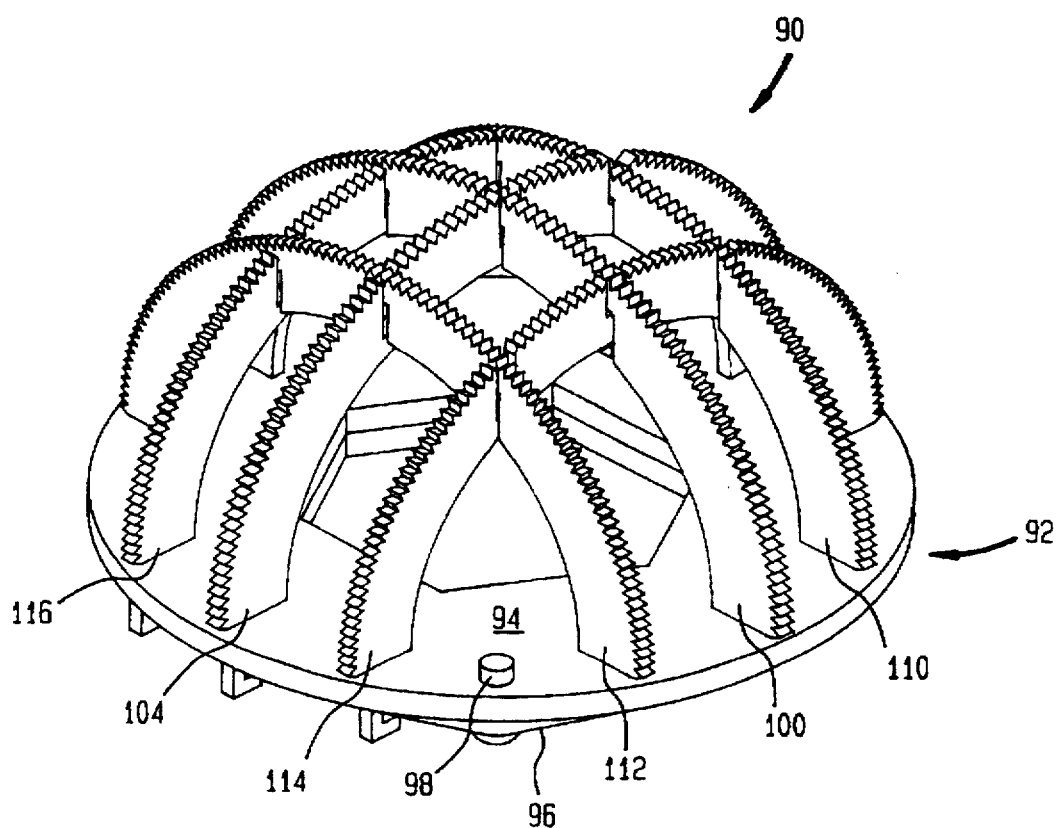
FIG. 7 is a perspective view of a second alternative embodiment of the invention which employs two base plates to lock the cutting blades in position.
Figure 8:
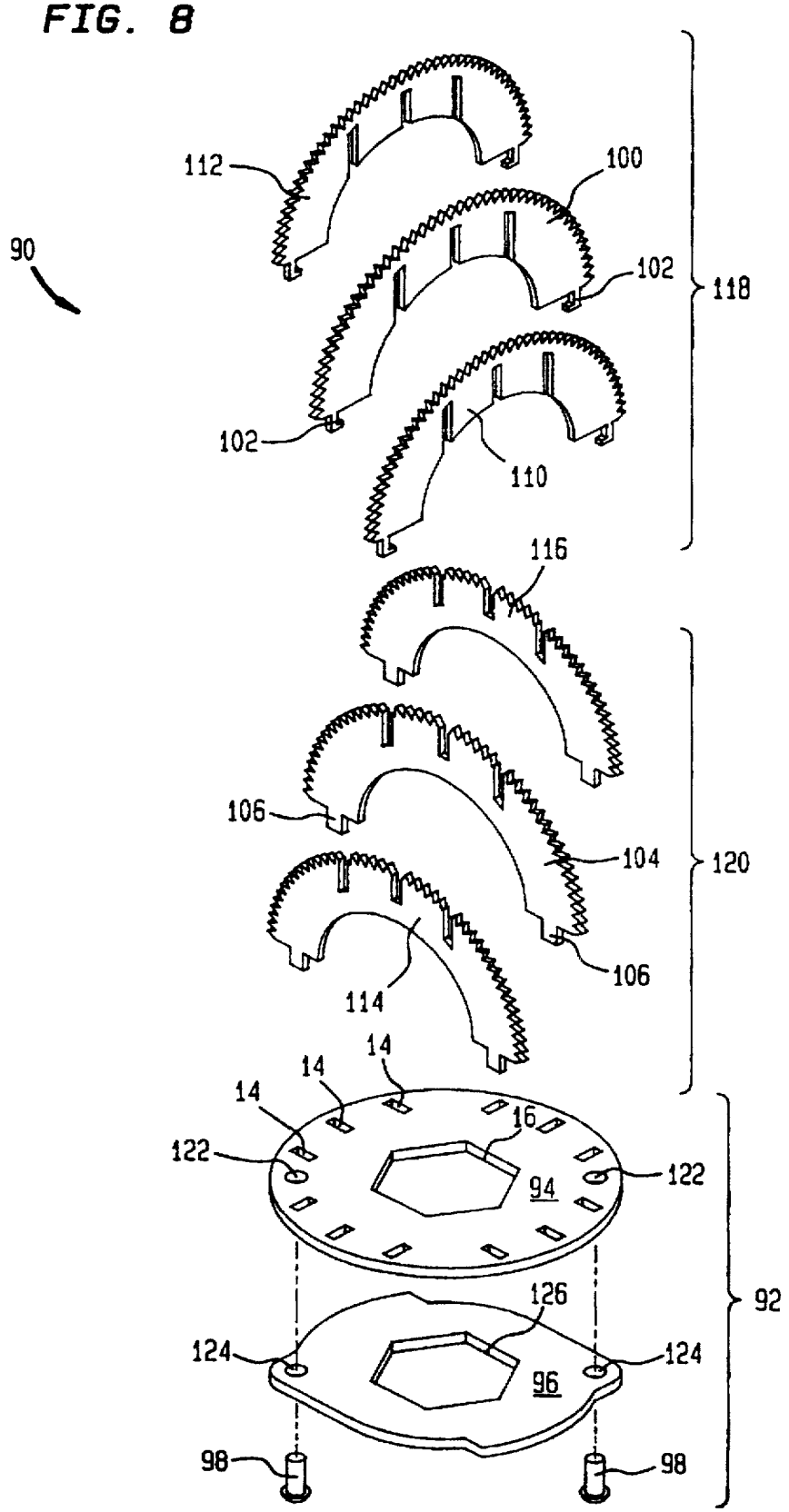
FIG. 8 is an exploded view of the second alternative embodiment of the invention illustrated in FIG. 7.
Figure 9:
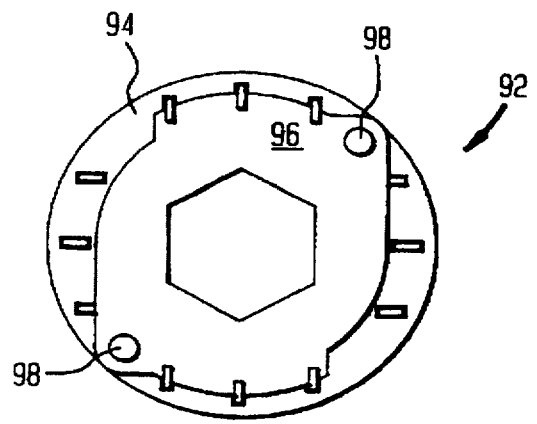
FIG. 9 is a bottom plan view showing the base of the second alternative embodiment of the invention as illustrated in FIGS. 7 and 8.
Figure 10A:
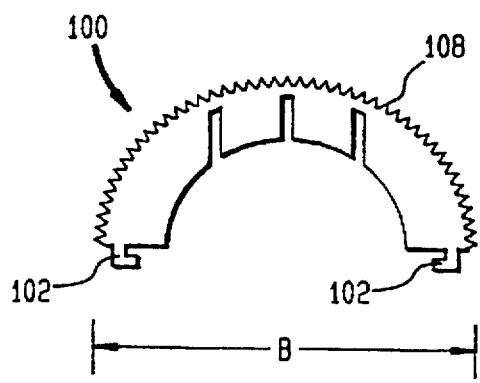
FIG. 10A illustrates a cutter blade having inwardly facing slots according to the second alternative embodiment of the invention illustrated in FIGS. 7–9.

A second alternative embodiment of the invention 90 is illustrated in assemble form in FIG. 7 and in an exploded view in FIG. 8. FIG. 9 illustrates the base 92 of the alternative embodiment 90 as seen from below. FIG. 10A illustrates the larger cutter blade 100 from the first group 120, whereas FIG. 10B illustrates the larger blade 104 from the second group 118.

The base 92 of the second preferred embodiment 90 includes a first upper base plate 94 and a second, lower, locking base plate 96. The first base plate 94 has a structure virtually identical to base plate 12 of the preferred embodiment 10 except that it includes a pair of rivet accepting holes 122. First base plate 94 also includes four sets of three slots 14 each positioned at 90° with respect to each other and a hexagonal central drive hole, or aperture, 16. The second, or lower locking plate 96, also includes a hexagonal shaped central drive hole 126 which lines up with drive hole 16 of the first plate 94. Locking plate 96 has a generally S-shaped configuration and has a pair of rivet accepting holes 124 which line up with holes 122 in the first, or upper, plate 94 when plates 94 and 96 are in proper alignment for locking the blades from the first and second sets 120 and 118. A pair of rivets 98 secures plates 94 and 96 together when holes 122 and 124 are properly aligned and then rivets 98 are swaged to lock plates 94 and 96 in rigid position.

The first set 120 of three blades 100, 110 and 112 can be more fully understood by referring to FIGS. 8 and 10a. The larger blade 100 is illustrated in FIG. 10A and is shown to include a pair of inwardly facing, L-shaped tabs 102 at the first and second ends thereof. Likewise, the smaller adjacent cutting blades 110 and 112 also include inwardly facing L-shaped tabs 102 similar to blade 100. Otherwise, the shape of the blades 100, 110 and 112 is similar to that of blades 20, 22 and 24 of group 18 of the preferred embodiment 10 illustrated in FIG. 1, in that they each include three inwardly facing slots.

Figure 10B:
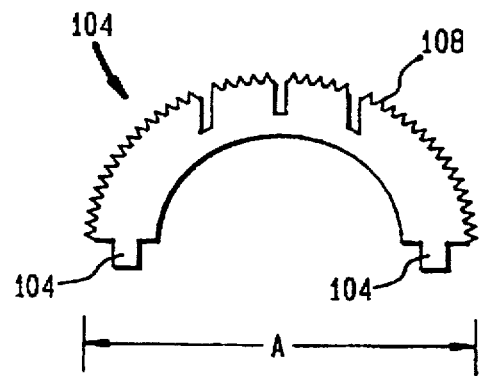
FIG. 10B illustrates another cutter blade having complimentary, outwardly facing slots, that mates with the blade of FIG. 10 and is suitable for use with the second alternative embodiment of the invention illustrated in FIGS. 7–9.

In contrast, the three blades 104, 114 and 116 of the second group 118 have a different tab 106 configuration as seen in FIGS. 8 and 10b. The larger cutter blade 104 of the group 118 is illustrated in FIG. 10B and is shown to include a pair of straight tabs 106 at the first and second end thereof. Tabs 106 do not have inwardly or outwardly facing projections and are shorter in length than the inwardly facing, L-shaped tabs 102 shown on blade 100 of FIG. 10A. Blades 114 and 116 also include short, stubby tabs 106 at the first and second ends thereof. Tabs 106 are intended to fit into peripheral slots 14 in the plate 94 but do not necessarily protrude all the way through. The purpose of tabs 106 is to hold blades 104, 114 and 116 of the second group 118 in position on plate 94. In contrast, the purpose of the L-shaped locking tabs 102 on blades 100, 110 and 112 of the first group 120 is to be engaged by the lower plate 96 and locked into position with respect to the base 92. Because the blades 100, 110 and 112 of the first group 120 are located above the blades 104, 114 and 116 of the second group 118, the blades of group 18 are automatically held in position even if they are not locked, i.e., anchored, directly with respect to base plate 94. As shown in FIGS. 10A and 10B, blades 100 and 104 (as well as 110, 112, 114 and 116) all include triangular cutting teeth 108. Lower blade 104 has a maximum outside diameter A in the range of 36 millimeters to 82 millimeters (1.417 to 3.228 inches). The upper major cutting blade 100 has a maximum exterior diameter B in the same range.

The second alternative embodiment 90 illustrated in FIGS. 8–10b is assembled in the following manner.

First, the nine outwardly facing slots in blades 104, 114 and 116 of second group 118 are aligned, at right angles, with the respectively inwardly facing slots of blades 100, 110 and 112 of first group 120, in a manner identical to that described with regard to the first step of the assembly of the preferred embodiment 10.

Second, the six loosely assembled blades are placed over first, upper base plate 94 so that all tabs 102 and 106 pass into their respective twelve receiving slots 14. As previously described, the stubby, shorter tabs 106 on blades 104, 114 and 116 of second group 18 do not necessarily pass all the way through their six respective receiving slots 14 in the first plate 94. Rather, the purpose of tabs 106 in peripheral slots 14 is to hold the blades into position rather than to lock them there. In contrast, the inwardly facing L-shaped tabs 106 on blades 100, 110 and 112 of second group 120 clearly pass through the bottom of the first, upper plate 94 enough so that all six of them can be engaged by the second, or lower locking plate, 96. There is enough of a gap in this configuration that locking plate 96 can be slid into the space between L-shaped tabs 102 and the upper, or first plate, 94 so that the tabs 102 cannot back out of slots 14. When properly in position, the rivet apertures 124 of the second lower plate 96 line up with, and are coaxial with, the rivet apertures 122 in the first plate 94.

Third, and last, a pair of rivets 98 is placed through coaxial holes 122 and 124 and swaged into position there so that plate 96 will permanently hold inwardly facing L-shaped tabs 102 in position in their respective six locking slots 14 in the first plate 94.

The second alternative embodiment 90 is significantly less expensive to manufacture and produce than prior art reamers. It is also very easy to assemble and can be put together in a satisfactory, permanent manner in a matter of minutes.

Figure 11A:
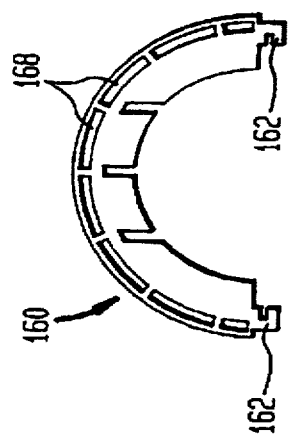
FIG. 11A illustrates a cutter blade having inwardly facing slots and including a cutting surface having oval cutouts.
Figure 11C:
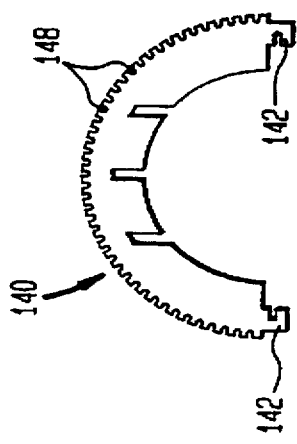
FIG. 11C illustrates a cutter blade having inwardly facing slots and having a cutting edge that comprises a plurality of teeth that are separated by semi-circular cutouts.
Figure 11E:
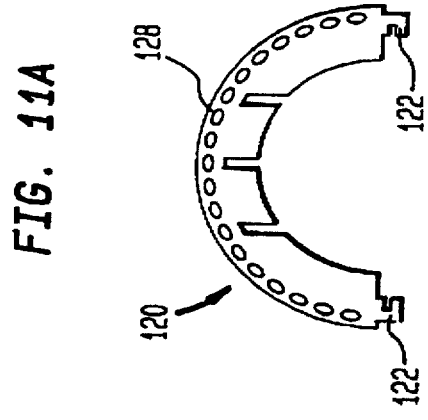
FIG. 11E illustrates a cutter blade having inwardly facing slots and having a cutting edge that includes a plurality of arcuate cutting slots.
Figure 11B:
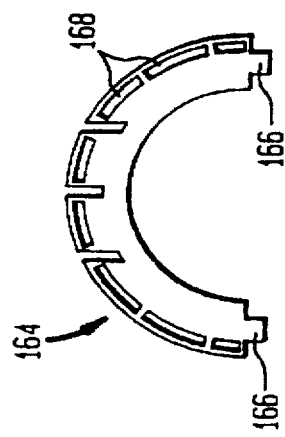
FIG. 11B illustrates a cutter blade having complimentary, outwardly facing slots, that mate with a blade of FIG. 11 also including oval cutouts that form its cutting surface.
Figure 11D:
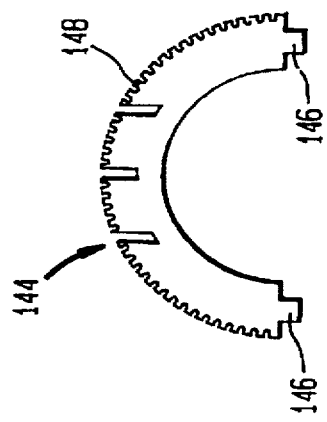
FIG. 11D illustrates a cutter blade having complimentary, outwardly facing slots, that mate with the blade of FIG. 11C also including a cutting edge that comprises a plurality of flat teeth separated by semi-circular cutout portions.
Figure 11F:
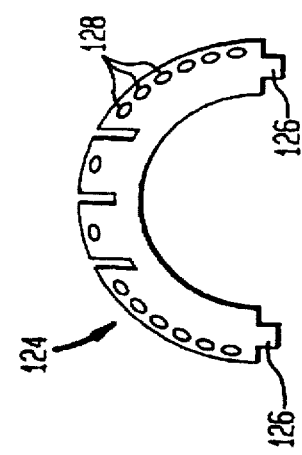
FIG. 11F illustrates a cutter blade having complimentary, outwardly facing slots that mate with the blade of FIG. 11E and also includes a cutting edge incorporating a plurality of arcuate cutting slots.

FIGS. 11A and 11B describe a pair of upper and lower blades 120 and 124 having a cutting edge that includes a plurality of oval cutout sections 128. Tabs 122 and 126 are employed for attachment to a base 92 as previously described. FIGS. 11C and 11D illustrate another pair of cutting blades 140 and 144 which include a cutting edge having a plurality of flat teeth 148 separated by semi-circular cutouts. As previously described, with regard to the embodiment of FIG. 11A and 11B, tabs 142 and 146 mate with base 92 such as illustrated in FIG. 8. Lastly, FIGS. 11E and 11F illustrate another pair of cutting blades 160 and 164 which include a plurality of arcuate cutting slots 168 on their cutting edge. Again, tabs 162 and 166 are intended to engage a base 92 such as illustrated in FIG. 8. While triangular teeth 108 such as illustrated in FIGS. 10A and 10B is the preferred cutting edge or surface, it is clear that a variety of other cutting topographies such as ovals 128, semi-circular cutout teeth 148 or arcuate slots 168 could be employed as well depending upon the nature of the cutting job to be performed.

In addition, modifications can be made to the base 92 as illustrated in the embodiment shown in FIG. 8. FIGS. 12A and 12B, respectively, illustrate the upper base plate 94 and the lower base plate 96 of the base 92 of embodiment 90. Upper plate 96 includes a hexagonal drive hole 16 having a dimension C of approximately 0.75 inches. Likewise, the lower base plate 96 includes a hexagonal drive aperture 126 having a dimension C also equal to 0.75 inches. Clearly, hexagonal drive hole 16 and 126 have identical shapes and dimensions. FIGS. 12C and 12D illustrate, respectively, an alternative upper base plate 194 and lower base plate 196. Upper base plate 194 includes a hexagonal central drive hole 16 having a dimension D of 1.018 inches. Likewise, the hexagonal central drive hole 126 of the lower base plate 196 also has a dimension D equal to 1.018 inches. The size of hexagonal drive hole 16 and 126 may vary depending upon the nature of the driving device and the material being reamed. Lastly, FIG. 12E and 12F, respectively, show an upper base plate 194 and a lower base plate 196. Upper base plate 294 includes an X-shaped central drive section 300 and four pie shaped cut out apertures 302 surrounding the X-shaped central section 300. Likewise, the lower base plate 296 includes an X-shaped central drive section 298 and four pie-shaped cutout apertures 290 surrounding the X-shaped central drive section 298. The cross arms of the X-shaped central drive sections 298 and 300 have a dimension E of approximately 0.195 inches. X-shaped cross-section 298 is substantially identical in shape and dimensions to X-shaped central drive section 300. The embodiments in FIGS. 12A–12F illustrate the fact that the variety of different, central drive sections may be employed depending upon the nature of the driving unit and the demand placed upon the reamer.

While the invention has been described with reference to the preferred embodiment thereof, it will be appreciated by those of ordinary skill in the art that modifications and changes can be made to the structure and function of the invention without departing from the spirit and scope thereof.

We claim:

1. An acetabular reamer apparatus comprising:
a base including a plurality of apertures therein;
a plurality of first blade means each including a first end with a projection thereon receivable in an aperture in said base, a second end distal from said first end and also including a projection thereon receivable in an aperture in said base, a first edge having a cutting surface thereon and including a slot means therein, and a second edge opposite from said first edge;
a plurality of second blade means each having a first end for contacting said base and a second end opposite from said first end and also for contacting said base, a first edge having a cutting surface thereon and a second edge opposite from said first edge including slot means therein,
wherein said slot means in said first blade means mate and engage with slot means in said second blade means and wherein said first and second blade means cross each other to form a three dimensional acetabular cutting surface when said apparatus is rotated.

2. The apparatus of claim 1 wherein said cutting surfaces on said blade means include cutting teeth.

3. The apparatus of claim 2 wherein said first blade means comprises at least two blades and said second blade means comprises at least two blades that cross said two blades of said first blade means substantially at right angles.

4. The apparatus of claim 3 wherein said first blade means comprises three blades and said second blade means comprises three blades that cross said three blades of said first blade means at right angles.

5. The apparatus of claim 4 wherein said base is substantially circular and includes a drive aperture in the center thereof.

6. The apparatus of claim 1 wherein said projections on said first and second blade means snap into said apertures in said base and automatically lock with respect thereto.

7. The apparatus of claim 1 wherein said projections on said first and second blade means can be inserted into said apertures in said base and twisted to lock said first and second blade means with respect to said base.

8. The apparatus of claim 1 wherein said base comprises:
a first plate having projection receiving apertures therein; and,
a second plate.
wherein attaching said second plate with respect to said first plate causes said projections to lock in position said first blade means with respect to said first plate.

9. The apparatus of claim 1 wherein said cutting surfaces on said blade means include a plurality of oval cutout sections.

10. The apparatus of claim 1 wherein said cutting surfaces on said blade means include a plurality of teeth separated by semi-circular cutout sections.

11. The apparatus of claim 1 wherein said cutting surfaces on said blade means includes a plurality of arcuate, cutting slots.

12. The apparatus of claim 1 wherein said base is substantially circular and includes a hexagonal drive aperture in the center thereof.

13. The apparatus of claim 1 wherein said base is substantially circular and includes an X-shaped, drive engaging section in the center thereof.

14. An acetabular reamer apparatus comprising:
a base;
a plurality of first blade means each having a first end attached to said base, a second end distal from said first end and also attached to said base, a first edge having a cutting surface thereon, and a second edge opposite from said first edge;
a plurality of second blade means each having a first end for contacting said base and a second end distal from said first end and also for contacting said base, a first edge having a cutting surface thereon and a second edge opposite from said first edge,
wherein said plurality of first and second blade means cross each other to form a three dimensional acetabular cutting surface when said apparatus is rotated.

15. An acetabular reamer apparatus comprising:
a base;
a plurality of first blade means each having a first end attached to said base, a second end distal from said first end and also attached to said base, a first edge having a cutting surface thereon, and a second edge opposite from said first edge;
a plurality of second blade means each having a first end for contacting said base and a second end distal from said first end and also for contacting said base, a first edge having a cutting surface thereon and a second edge opposite from said first edge,
wherein said plurality of first and second blade means cross each other at substantially right angles to form a three dimensional acetabular cutting surface when said apparatus is rotated.

* * * * *